US008513141B2

(12) United States Patent
Souriau et al.

(10) Patent No.: US 8,513,141 B2
(45) Date of Patent: Aug. 20, 2013

(54) DEFECT ETCHING OF GERMANIUM

(75) Inventors: Laurent Souriau, Heverlee (BE); Valentina Terzieva, Bertem (BE)

(73) Assignee: IMEC, Leuven (BE)

( * ) Notice: Subject to any disclaimer, the term of this patent is extended or adjusted under 35 U.S.C. 154(b) by 13 days.

(21) Appl. No.: 13/275,415

(22) Filed: Oct. 18, 2011

(65) Prior Publication Data
US 2012/0034787 A1    Feb. 9, 2012

Related U.S. Application Data

(62) Division of application No. 12/362,045, filed on Jan. 29, 2009, now abandoned.

(30) Foreign Application Priority Data

Jan. 31, 2008 (EP) ...................................... 08150895

(51) Int. Cl.
*H01L 21/302* (2006.01)
(52) U.S. Cl.
USPC ............................. 438/745; 438/752; 216/88
(58) Field of Classification Search
USPC .................. 438/750, 703, 587, 20, 399, 746; 205/655; 257/183; 216/88, 83, 13; 355/133; 428/472.1; 429/111; 560/176; 516/56; 430/430, 413
See application file for complete search history.

(56) References Cited

U.S. PATENT DOCUMENTS

| 3,576,631 | A | | 4/1971 | Archambault et al. |
| 4,294,651 | A | | 10/1981 | Ohmura |
| 4,971,654 | A | | 11/1990 | Schnegg et al. |
| 5,695,556 | A | * | 12/1997 | Tamamura et al. ............. 117/85 |
| 6,605,548 | B1 | * | 8/2003 | Bardwell ....................... 438/745 |
| 2002/0013064 | A1 | * | 1/2002 | Bang ............................. 438/746 |
| 2002/0142619 | A1 | | 10/2002 | Grabbe et al. |
| 2004/0076813 | A1 | * | 4/2004 | Han et al. .................... 428/312.6 |
| 2005/0169096 | A1 | | 8/2005 | Lee et al. |
| 2006/0032836 | A1 | | 2/2006 | Feng et al. |
| 2006/0144823 | A1 | | 7/2006 | Kim et al. |

FOREIGN PATENT DOCUMENTS

| DE | 1068840 B | 11/1958 |
| EP | 0182306 A2 | 5/1986 |
| JP | 11-001781 | 1/1999 |

(Continued)

OTHER PUBLICATIONS

Plummer et al. Silicon VLSI Technology, published by Tom Robbins, 2000, p. 612-618 (Plummer).*

(Continued)

*Primary Examiner* — Duy Deo
*Assistant Examiner* — Erin Bergner
(74) *Attorney, Agent, or Firm* — McDonnell Boehnen Hulbert & Berghoff LLP

(57) ABSTRACT

The present invention provides an etching solution for revealing defects in a germanium layer, a method for revealing defects in a germanium layer using such an etching solution and to a method for making such an etching solution. The etching solution according to embodiments of the present invention is able to exhibit an etch rate of between 4 nm·min$^{-1}$ and 450 nm·min$^{-1}$, which makes it suitable to be used for revealing defects in a thin layer of germanium, i.e. in a layer of germanium with a thickness of between 20 nm and 10 μm, for example between 20 nm and 2 μm, between 20 nm and 1 μm or between 20 nm and 200 nm.

16 Claims, 4 Drawing Sheets

(56) References Cited

FOREIGN PATENT DOCUMENTS

| WO | 00/72374 A1 | 11/2000 |
|---|---|---|
| WO | 02/054155 A1 | 7/2002 |
| WO | 2004/112122 A1 | 12/2004 |
| WO | 2005/024927 A1 | 3/2005 |

OTHER PUBLICATIONS

Baca et al., Fabrication of GaAs Devices, 2005, Institution of Engineering and Technology, Chapter 4 Wet etching and photolithography of GaAs and related alloys, pp. 117-120.*

Dale, J.R., et al., "Etch Pits in Germanium and Their Relation to Hardness", Solid-State Electronica, Feb. 1961, pp. 105-109, vol. 3, Pergamon Press, Great Britain.

Pfann, W.G., et al., "Observations on the Dislocation Structure of Germanium Crystals", ACTA Metallurgica, 1957, pp. 377-384, vol. 5.

Souriau, L., et al., "A Wet Etching Technique to Reveal Threading Dislocations in Thin Germanium Layers", Solid State Phenomena, 2008, pp. 83-86, vol. 134, Trans Tech Publications, Switzerland.

Jenkins, M., "A New Preferential Etch for Defects in Silicon Crystals", J. Electrochem. Soc.: Solid-State Science and Technology, May 1977, pp. 757-762, vol. 124, No. 5.

Gorokhov, E.B., "Resolution of Dislocation Lines in Germanium by Etching", Neorganischeski Materialy, vol. 18, No. 6, Jun. 1982, pp. 885-889, XP008093789 Plenum Publishing Corporation.

Calzecchi, F. et al., "Identification of the Dislocation Type in Germanium by Means of Etch Pits", IL Nuovo Cimento, vol. XLVB, No. 1, Sep. 1966, pp. 226-228, XP008093791, Italy.

Interuniversitair Microelektronica Centrum VZW (IMEC), European Search Report, Application No. EP 08 15 0895.4-2122, Jul. 11, 2008.

Van De Ven, J., et al., "Kinetics and Morphology of GaAs Etching in Aqueous CrO3-HF Solutions", J. Electrochem. Soc.: Solid-State Science and Technology, Apr. 1986, pp. 799-806.

Plummer, et al., Silicon VLSI Technology, published by Tom Robbins, 2000 pp. 612-618.

* cited by examiner

US 8,513,141 B2

DEFECT ETCHING OF GERMANIUM

CROSS-REFERENCE TO RELATED APPLICATIONS

This application is a divisional application of U.S. patent application Ser. No. 12/362,045, filed Jan. 29, 2009, which claims priority to European patent application number 08150895.4 filed on Jan. 31, 2008, the disclosures of which are incorporated herein by reference in their entirety.

TECHNICAL FIELD OF THE INVENTION

The present invention relates to defect etching of germanium. More particularly, the present invention relates to an etching solution for revealing defects in a germanium layer, to a method for revealing defects in a germanium layer using such an etching solution and to a method for making such an etching solution. The method and solution according to embodiments of the invention is environmentally and user friendly.

BACKGROUND OF THE INVENTION

For decades, performance enhancement of microelectronic chips has been obtained by scaling down feature size of silicon (Si) single devices resulting in a concomitant improvement of the drive current and an increase of device density. However, because this strategy finds its limits around the 22 nm node, new channel materials like e.g. germanium (Ge) with intrinsically higher mobility than Si have to be introduced to further improve efficiency of circuits.

Because of the low availability of Ge on earth, it is most likely that mass production will occur on hybrid substrates where only a thin Ge layer is present on a Si substrate serving as mechanical support. For example, Ge can be deposited epitaxially on Si by chemical vapor deposition (CVD). However, because of the large 4% lattice mismatch between the two materials, coherent growth is only limited to less than 1 nm. Convenient layers are always thicker and thus present strain relaxation which mainly occurs via the formation of misfit dislocations at the interface between Si and Ge. These misfit dislocations can terminate at the edge of the wafer but often penetrate through the Ge film and end at the surface as a threading dislocation. It is crucial to avoid defects because of their adverse effects on the electrical performance of devices but also on their reliability.

Therefore, characterization techniques are needed to monitor their density and distribution so as to develop growth techniques minimizing the occurrence of such defects. Unlike, for example, Transmission Electron Microscopy (TEM) or Electron Beam Induced Current (EBIC), defect etching is a simple, fast and low cost technique to assess crystal quality of materials (see M. W Jenkins, J. Electrochem. Soc., Volume 124, Issue 5 (1977), 757-762).

Wet etching of semiconductor materials is usually conducted in a three component chemical mixture comprising an oxidizing agent that oxidizes semiconductor surface atoms (e.g. $HNO_3$, $H_2O_2$, $O_3$, $Br_2$, $CrO_3$, $K_2Cr_2O_7$), a complexing agent that dissolves the oxide that is formed on the surface (e.g. HF) and a solvent for dilution (e.g. $H_2O$, $CH_3COOH$) (see M. W Jenkins, J. Electrochem. Soc., Volume 124, Issue 5 (1977), 757-762). In the case of defect etching the overall reaction is sensible to the presence of defects at the surface, i.e. it is sensible to the difference in stress level and/or composition variation so that the etching proceeds faster or slower at the defect site than in the perfect crystal, or in other words at locations where no defects are present. As a consequence, because the surface is originally relatively smooth before etching, some topography (e.g. pit or hillock) is created on the etched surface and the defects are rendered visible. Microscopy techniques such as Scanning Electron Microscopy (SEM) or Atomic Force Microscopy (AFM) then allow observation of the etched surface and the determination of the nature of defects and their density.

For Ge, depending on the surface orientation of the substrates (100, 110 or 111) some solutions are available for the revelation of threading dislocations. However, the etch rate of these solutions is in the order of a few $\mu m \cdot min^{-1}$ which renders the revelation of defects in thin layers impossible. By diluting the solutions, the etch rate may be decreased but the selectivity towards defects is also drastically decreased. As a result, the overall process shifts from a surface reaction controlled regime to a mass controlled regime, or in other words, from a defect preferential etching to a polishing etching which makes it impossible to reveal the defects.

In "L. Souriau, V. Terzieva, M. Meuris and M. Caymax, Solid State Phenomena Vol. 134 (2008), 83-86" a solution is described for revealing threading dislocations in thin Ge layers. The solution described in this document is based on a $CrO_3/HF/H_2O$ system which was also extensively described for Si and GaAs (see J van de Ven, J. L. Weyher, J. E. A. M. van den Meerakker and J. J. Kelly, J. Electrochem. Soc., Volume 133, Issue 4, (1986), 799-806). The solution exhibits a low etch rate of between 7 and 100 $nm \cdot min^{-1}$ depending on the doping, strain state and surface orientation of the Ge layer. It has a good selectivity towards defects. With this solution it is possible to reveal dislocations on (100) and (111) oriented Ge.

A disadvantage of the $CrO_3/HF/H_2O$ solution described in these documents is that it makes use of carcinogenic $Cr^{VI}$ together with HF acid, which makes it environmentally and user unfriendly.

SUMMARY OF THE INVENTION

It is an object of embodiments of the present invention to provide an etching solution for revealing defects in a III-V semiconductor layer or a germanium layer, a method for revealing defects in a III-V semiconductor layer or a germanium layer, using such an etching solution and to a method for making such an etching solution.

The above objective is accomplished by a method and device according to the present invention.

The method and solution according to embodiments of the invention are environmentally and user friendly. They do not make use of carcinogenic substances. Etching solutions according to embodiments of the present invention do not require addition of HF.

Because of the low etch rate, the method and solution according to embodiments of the invention can advantageously be used for revealing defects in thin III-V semiconductor layers or thin Ge layers, i.e. in III-V semiconductor layers or Ge layers having a thickness of between 20 nm and 10 $\mu m$, for example between 20 nm and 2 $\mu m$, between 20 nm and 1 $\mu m$ or between 20 nm and 200 nm.

In a first aspect, the present provides an etching solution for revealing defects in a germanium layer. The solution comprises:
  an oxidizing agent comprising $Ce^{4+}$ or $MnO_4^-$, and
  a solvent such as e.g. water.

The etching solution is able to exhibit an etch rate of between 4 $nm \cdot min^{-1}$ and 450 $nm \cdot min^{-1}$.

In another aspect of the invention, the present provides an etching solution for revealing defects in a III-V semiconductor layer, e.g. a layer comprising GaAs or InP or a combination thereof such as e.g. GaInAs or GaInP. The solution comprises:

an oxidizing agent comprising $Ce^{4+}$ or $MnO_4^-$, and
a solvent such as e.g. water.

The etching solution is able to exhibit an etch rate of between 4 nm·min$^{-1}$ and 450 nm·min$^{-1}$.

It is an advantage of the etching solution according to embodiments of the invention that it does not comprise carcinogenic $Cr^{VI}$. It is furthermore an advantage of the etching solution according to embodiments of the invention that it does not require the use of hydrofluoric acid (HF). Because of the absence of $Cr^{VI}$ and optionally of HF, the etching solution according to embodiments of the present invention is environmentally and user friendly. Because of the low etching rate of between 4 nm·min$^{-1}$ and 450 nm·min$^{-1}$ the etching solution according to embodiments of the invention may be used for revealing defects in thin germanium layers, i.e. in germanium layers with a thickness of between 20 nm and 10 µm, for example between 20 nm and 2 µm, between 20 nm and 1 µm or between 20 nm and 200 nm.

The solvent may, for example, be water or another polar protic solvent such as e.g. formic acid, ethanol or methanol.

According to embodiments of the invention, the etch rate may be between 4 nm·min$^{-1}$ and 200 nm·min$^{-1}$ or between 4 nm·min$^{-1}$ and 100 nm·min$^{-1}$.

The lower the etch rate is, the better the etch process can be controlled and the more suitable the etching solution according to embodiments of the invention is when it is to be used for revealing defects, e.g. threading dislocations, in thin Ge layers or thin III-V semiconductor layers, with a thickness of between 20 nm and 10 µm, for example between 20 nm and 2 µm, between 20 nm and 1 µm or between 20 nm and 200 nm.

The oxidizing agent may be a component able to, when forming part of an etching solution according to embodiments of the present invention, provide characteristics to the etching solution such that the etching solution:

provides an etch rate of between 4 nm·min$^{-1}$ and 450 nm·min$^{-1}$, between 4 nm·min$^{-1}$ and 200 nm·min$^{-1}$ or between 4 nm·min$^{-1}$ and 100 nm·min$^{-1}$, and
provides a selectivity towards defects of 1 or higher, for example 5 or higher.

According to embodiments of the invention, the etching solution may comprise $Ce^{4+}$.

$Ce^{4+}$ may be present in a concentration of between 0.01 mol·L$^{-1}$ and 1 mol·L$^{-1}$, for example the $Ce^{4+}$-concentration may be lower than 0.4 mol·L$^{-1}$.

According to other embodiments of the invention, the etching solution may comprise $MnO_4^-$.

$MnO_4^-$ may be present in a concentration of between 0.01 mol·L$^{-1}$ and 0.6 mol·L$^{-1}$.

According to embodiments of the invention, the etching solution may furthermore comprise HF. The presence of HF may increase the etch rate but does not change or does not substantially change the selectivity of the etching solution.

HF may be present in a concentration of between 0 mol·L$^{-1}$ and 5 mol·L$^{-1}$.

Because HF is present in a relatively low concentration compared to prior art solutions, the etching solution, although comprising quantities of HF according to embodiments of the present invention, may still be more environmentally and user friendly than the prior art methods using HF.

An etching solution according to embodiments of the invention may have a selectivity towards the defects of 1.

The present invention also provides the use of an etching solution according to embodiments of the invention for revealing defects in a thin germanium layer with a thickness of between 20 nm and 10 µm, for example between 20 nm and 2 µm, between 20 nm and 1 µm or between 20 nm and 200 nm.

The present invention also provides the use of an etching solution according to embodiments of the invention for revealing defects in a thin III-V semiconductor layer, e.g. a layer comprising GaAs or InP or a combination thereof such as e.g. GaInAs or GaInP, with a thickness of between 20 nm and 10 µm, for example between 20 nm and 2 µm, between 20 nm and 1 µm or between 20 nm and 200 nm.

In a further aspect, the present invention provides a method for making an etching solution for revealing defects in a germanium layer, the etching solution being able to exhibit an etch rate of between 4 nm·min$^{-1}$ and 450 nm·min$^{-1}$, or between 4 nm·min$^{-1}$ and 200 nm·min$^{-1}$ or between 4 nm·min$^{-1}$ and 100 nm·min$^{-1}$. The method comprises:

providing an oxidizing agent comprising $Ce^{4+}$ or $MnO_4^-$ in a container and
adding a solvent.

In yet a further aspect, the present invention provides a method for making an etching solution for revealing defects in a III-V semiconductor layer, e.g. a layer comprising GaAs or InP or a combination thereof such as e.g. GaInAs or GaInP, the etching solution being able to exhibit an etch rate of between 4 nm·min$^{-1}$ and 450 nm·min$^{-1}$, or between 4 nm·min$^{-1}$ and 200 nm·min$^{-1}$ or between 4 nm·min$^{-1}$ and 100 nm·min$^{-1}$. The method comprises:

providing an oxidizing agent comprising $Ce^{4+}$ or $MnO_4^-$ in a container and
adding a solvent.

Adding a solvent may, for example, be performed by adding water or another polar protic solvent such as e.g. formic acid, ethanol or methanol.

According to embodiments of the invention, providing an oxidizing agent may be performed by providing an oxidizing agent comprising $Ce^{4+}$.

$Ce^{4+}$ may be provided in a concentration of between 0.01 mol·L$^{-1}$ and 1 mol·L$^{-1}$.

According to other embodiments of the invention, providing an oxidizing agent may be performed by providing an oxidizing agent comprising $MnO_4^-$.

$MnO_4^-$ may be provided in a concentration of between 0.01 mol·L$^{-1}$ and 0.6 mol·L$^{-1}$.

The method may furthermore comprise adding HF to the etching solution. Adding HF may increase the etch rate of the etching solution but does not or not substantially change the selectivity of the etching solution.

HF may be provided in a concentration of between 0 mol·L$^{-1}$ and 5 mol·L$^{-1}$.

The present invention also provides an etching solution for revealing defects in a germanium layer, the etching solution being made by a method according to embodiments of the invention.

The present invention also provides an etching solution for revealing defects in a III-V semiconductor layer, e.g. a layer comprising GaAs or InP or a combination thereof such as e.g. GaInAs or GaInP, the etching solution being made by a method according to embodiments of the invention.

In yet a further aspect, the present invention provides a method for revealing defects in a germanium layer. The method comprises immersing a substrate comprising the germanium layer in an etching solution comprising an oxidizing agent comprising $Ce^{4+}$ or $MnO_4^-$, and a solvent, the etching solution being able to exhibit an etch rate of between 4 nm·min$^{-1}$ and 450 nm·min$^{-1}$ or between 4 nm·min$^{-1}$ and 200 nm·min$^{-1}$ or between 4 nm·min$^{-1}$ and 100 nm·min$^{-1}$.

In still a further aspect, the present invention provides a method for revealing defects in a III-V semiconductor layer, e.g. a layer comprising GaAs or InP or a combination thereof such as e.g. GaInAs or GaInP. The method comprises immersing a substrate comprising the III-V semiconductor layer, e.g. a layer comprising GaAs or InP or a combination thereof such as e.g. GaInAs or GaInP, in an etching solution comprising an oxidizing agent comprising $Ce^{4+}$ or $MnO_4^-$, and a solvent, the etching solution being able to exhibit an etch rate of between 4 nm·min$^{-1}$ and 450 nm·min$^{-1}$ or between 4 nm·min$^{-1}$ and 200 nm·min$^{-1}$ or between 4 nm·min$^{-1}$ and 100 nm·min$^{-1}$.

Immersing the substrate comprising the Ge layer or the III-V semiconductor layer, e.g. a layer comprising GaAs or InP or a combination thereof such as e.g. GaInAs or GaInP, in the etching solution may be performed during a time period of between 1.5 minutes and 10 minutes, depending on the concentration of oxidizing agent present in the etching solution.

Particular and preferred aspects of the invention are set out in the accompanying independent and dependent claims. Features from the dependent claims may be combined with features of the independent claims and with features of other dependent claims as appropriate and not merely as explicitly set out in the claims.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
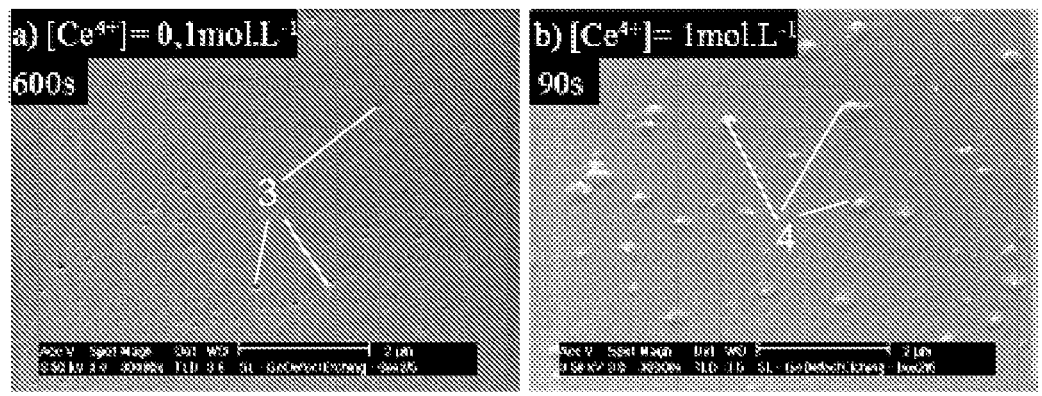
FIG. 1 illustrates SEM images of a 1.5 μm Ge layer on Si(100) after etching in (a) a $Ce^{4+}/H_2O$ solution according to embodiments of the present invention comprising 0.1 mol·L$^{-1}$ for 10 minutes and (b) a $Ce^{4+}/H_2O$ solution according to embodiments of the present invention comprising 1 mol·L$^{-1}$ for 1.5 minutes.

In the different figures, the same reference signs refer to the same or analogous elements.

DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practised without these specific details. In other instances, well-known methods, structures and techniques have not been shown in detail in order not to obscure an understanding of this description.

The invention will now be described by a detailed description of several embodiments of the invention. It is clear that other embodiments of the invention can be configured according to the knowledge of persons skilled in the art without departing from the technical teaching of the invention, the invention being limited only by the terms of the appended claims.

The present invention provides an etching solution for revealing defects in a germanium layer, a method for revealing defects in a germanium layer using such an etching solution and a method for making such an etching solution.

The etching solution comprises:
an oxidizing agent comprising $Ce^{4+}$ or $MnO_4^-$, and
a solvent,
the etching solution being able to exhibit an etch rate of between 4 nm·min$^{-1}$ and 450 nm·min$^{-1}$.

The solvent may, for example, be water or another polar protic solvent such as for example a carboxylic acid (e.g. formic acid or acetic acid). The solvent should not be too reactive when mixed with the oxidizing agent. Carboxylic acids are already in an oxidized form so that they are less reactive with the oxidizing agent than, for example, alcohols such as ethanol or methanol which, when mixed with a strong oxidising agent, will oxidize to form their carbonyl counterpart.

According to embodiments of the invention, the etch rate may be between 4 nm·min$^{-1}$ and 200 nm·min$^{-1}$, or between 4 nm·min$^{-1}$ and 100 nm·min$^{-1}$.

The etching solution according to embodiments of the invention does not comprise carcinogenic $Cr^{VI}$ or other carcinogenic substances, as is the case for prior art solutions. Furthermore the etching solution according to embodiments of the invention does not require the use of hydrofluoric acid (HF). Because of the absence of $Cr^{VI}$ and optionally of HF, the etching solution according to embodiments of the present invention is environmentally and user friendly. In other embodiments, the etching solution does comprise some HF, but less than prior art solutions, thus being more environmentally and user friendly than these prior art solutions.

Because of the low etching rate of between 4 nm·min$^{-1}$ and 450 nm·min$^{-1}$ the etching solution according to embodiments of the invention may be used for revealing defects in thin germanium layers, i.e. in germanium layers with a thickness of between 20 nm and 10 μm, for example between 20 nm and 2 μm, between 20 nm and 1 μm or between 20 nm and 200 nm. The oxidizing agent may be a component able to, when part of an etching solution according to embodiments of the present invention:

provide to the etching solution an etch rate of between 4 nm·min$^{-1}$ and 450 nm·min$^{-1}$, between 4 nm·min$^{-1}$ and 200 nm·min$^{-1}$ or between 4 nm·min$^{-1}$ and 100 nm·min$^{-1}$, and provide to the etching solution a selectivity towards defects of 1 or higher, for example 5 or higher.

According to a first embodiment of the present invention, the etching solution may comprise $Ce^{4+}$ as an oxidizing agent and water as a solvent. Hence, the etching solution according to this first embodiment may be referred to as a $Ce^{4+}/H_2O$ solution. As a source for $Ce^{4+}$, for example cerium ammonium nitrate $((NH_4)_2Ce(NO_3)_6)$ may be used because it has a high solubility of 141 g/100 ml in water at 25° C. However, according to other embodiments, also other $Ce^{4+}$-sources can be used, such as e.g. but not limited to Ammonium Cerium Sulphate $Ce(NH_4)_4(SO_4)_4$ or Cerium sulphate $Ce(SO_4)_2$, as long as they can easily be dissolved in water. The etching solution according to the first embodiment may comprise $Ce^{4+}$ in a concentration of between 0.01 mol·L$^{-1}$ and 3 mol·L$^{-1}$, for example between 0.01 mol·L$^{-1}$ and 1 mol·L$^{-1}$ or between 0.01 mol·L$^{-1}$ and 0.4 mol·L$^{-1}$. It has to be noted that the etch rate of the solution increases with increasing concentration of $Ce^{4+}$. Hence, a suitable $Ce^{4+}$ concentration may be chosen as a function of the desired etch rate.

Hereinafter, the etching solution according to the first embodiment will further be described by means of some experiments. For these experiments, different amounts of $(NH_4)_2Ce(NO_3)_6$ were dissolved in $H_2O$ so as to obtain different etching solutions with different $Ce^{4+}$-concentration. Etching was carried out at a 1.5 μm thick Ge layer on Si(100) and was performed by dipping 2×2 cm$^2$ samples in a beaker containing the etching solution. The solutions were always freshly prepared, unless otherwise mentioned. The samples were partially immersed in the etching solution so as to produce a step which was used for the determination of the etch rate (ER). No stirring was applied to the solutions during etching and all experiments were done at room temperature. After etching, the samples were thoroughly rinsed with deionized water (DIW) in order to immediately stop all reactions but also to clean the etched surface before further characterization. The samples were subsequently dried under $N_2$ flow. Scanning electron microscopy (SEM) was used as a characterization technique. Imaging of the etched surfaces before and after etching was done in a 45° tilted geometry whereas etch rate measurement was performed by doing cross-section measurements in the etched and non-etched regions.

The defect etching capability of the $Ce^{4+}/H_2O$ solution according to the first embodiment was examined for $Ce^{4+}$-concentrations ranging from 0.01 mol·L$^{-1}$ to 1 mol·L$^{-1}$. Typical examples of SEM and AFM images of the Ge surface after etching are respectively illustrated in FIG. 1 and FIG. 2, thereby illustrating the advantages of the $Ce^{4+}/H_2O$ solution according to the first embodiment to reveal defects, e.g. threading dislocations, in germanium.

FIG. 1 shows a SEM picture of the 1.5 μm thick Ge layer on Si(100) after etching in $Ce^{4+}/H_2O$ solutions with different $Ce^{4+}$-concentrations and for different times. FIG. 1(a) shows a Ge layer after etching for 10 minutes in a $Ce^{4+}/H_2O$ solution comprising 0.1 mol·L$^{-1}$ $Ce^{4+}$. FIG. 1(b) shows a Ge layer after etching for 1.5 minutes in a $Ce^{4+}/H_2O$ solution comprising 1 mol·L$^{-1}$ $Ce^{4+}$. It has been found that, depending on the concentration of $Ce^{4+}$ ions in the solution, the morphology of the Ge surface after etching is different. Etch pits are observed for a $Ce^{4+}$-concentration lower than 0.4 mol·L$^{-1}$ while hillocks are observed for $Ce^{4+}$-concentration of 0.4 mol·L$^{-1}$ and higher.

Figure 2:
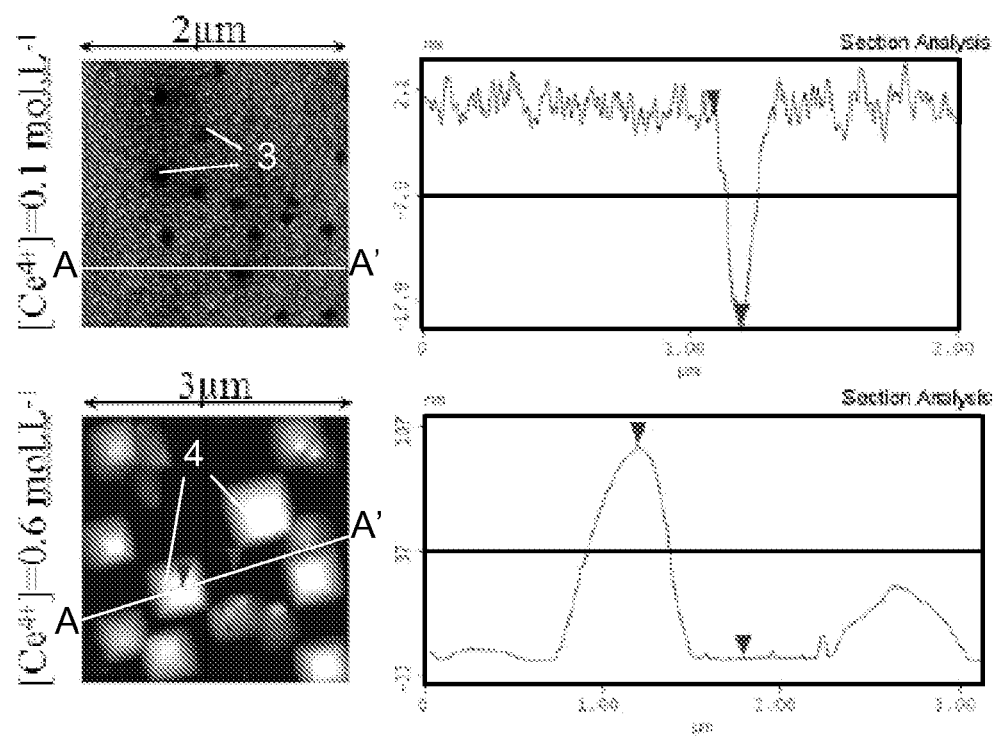
FIG. 2 shows Atomic Force Microscopy (AFM) images (left part) and their respective tip trace through the etch figure (pit or hillock) after etching of a 1.5 μm thick Ge layer on Si(100) in a $Ce^{4+}/H_2O$ solution according to embodiments of the present invention comprising 0.1 mol·L$^{-1}$ (upper part) and after etching of a 1.5 μm thick Ge layer on Si(100) in a $Ce^{4+}/H_2O$ solution according to embodiments of the present invention comprising 0.6 mol·L$^{-1}$ (lower part).

FIG. 2 shows an AFM picture of the Ge layer after etching in a $Ce^{4+}/H_2O$ solution comprising 0.1 mol·L$^{-1}$ $Ce^{4+}$ (see upper part of FIG. 2) and in a $Ce^{4+}/H_2O$ solution comprising 0.6 mol·L$^{-1}$ $Ce^{4+}$ (see lower part of FIG. 2) together with their respective tip trace through the AFM figure along the line AA'. In case of the $Ce^{4+}/H_2O$ solution comprising 0.1 mol·L$^{-1}$ $Ce^{4+}$ square pyramidal etch pits 3 are formed at the surface of the Ge layer during etching whereas in case of the $Ce^{4+}/H_2O$ solution comprising 0.6 mol·L$^{-1}$ $Ce^{4+}$ square pyramidal hillocks 4 are formed at the surface of the Ge layer during etching. The difference in surface morphology, i.e. the formation of etch pits 3 or hillocks 4 when using solutions with different $Ce^{4+}$-concentrations can be explained as follows. At $Ce^{4+}$-concentrations of 0.4 $mol \cdot L^{-1}$ or higher some insoluble tetragonal $GeO_2$ oxide may be produced on the core of the defects, e.g. threading dislocations, which may prevent further etching at that point and which then may lead to the formation of the hillocks 4.

Figure 3:
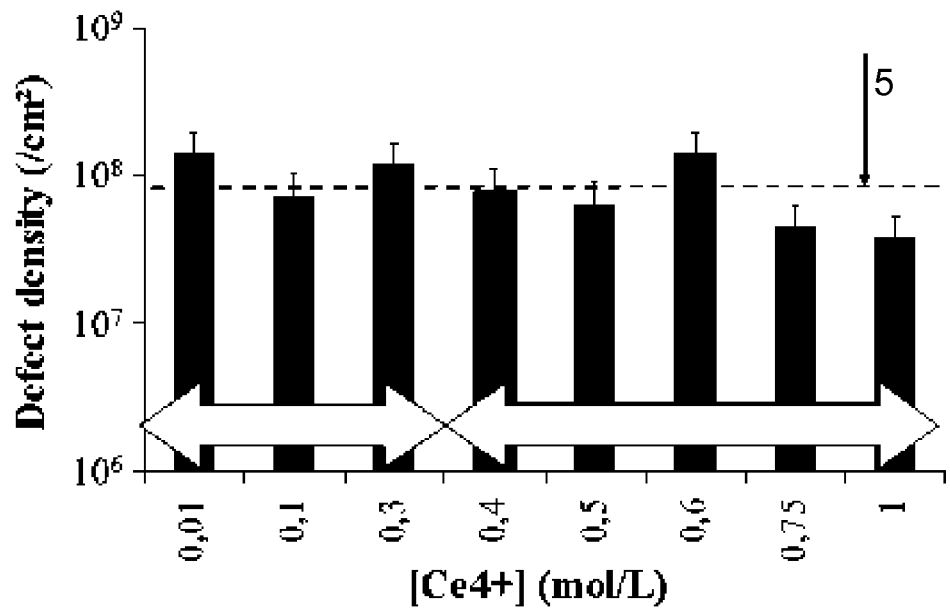
FIG. 3 shows the threading dislocation density for a 1.5 μm thick Ge layer after etching in $Ce^{4+}/H_2O$ solutions according to embodiments of the present invention with different $Ce^{4+}$-concentrations.

The threading dislocation density (TDD) has been determined for different $Ce^{4+}$-concentrations between 0.01 $mol \cdot L^{-1}$ and 1 $mol \cdot L^{-1}$ (see FIG. 3). Etching time has been adapted for the different concentrations in order to prevent removal of the entire Ge layer. Therefore, the Ge layer was etched for 10 min in $Ce^{4+}/H_2O$ solutions comprising between 0.01 $mol \cdot L^{-1}$ and 0.3 $mol \cdot L^{-1}$, for 3 min in $Ce^{4+}/H_2O$ solutions comprising between 0.4 $mol \cdot L^{-1}$ and 0.75 $mol \cdot L^{-1}$ and for 1.5 min in $Ce^{4+}/H_2O$ solutions comprising 1 $mol \cdot L^{-1}$. From FIG. 3 it can be seen that for all $Ce^{4+}$-concentrations between 0.01 $mol \cdot L^{-1}$ and 1 $mol \cdot L^{-1}$ approximately a same defect density of $10^8/cm^2$ was obtained.

For the sake of comparison, the dashed line indicated with arrow 5 in FIG. 3 indicates a TDD of $8 \cdot 10^7/cm^2$ obtained with a prior art $CrO_3/HF/H_2O$ solution. This shows that the TDD obtained with the $Ce^{4+}/H_2O$ solution according to the first embodiments of the present invention agrees well within experimental errors (indicated by I in FIG. 3) with the value determined by defect etching with the prior art $CrO_3/HF/H_2O$ solution or by cross-section TEM. Thus, although the etching solution according to the first embodiments of the invention does not comprise carcinogenic $Cr^{VI}$ nor HF, it leads to comparable results as the prior art solution comprising $Cr^{VI}$ as well as HF.

The results obtained and described above thus demonstrate that the $Ce^{4+}/H_2O$ solution according to the first embodiment of the invention can be used to perform defect etching of Ge without using carcinogenic $Cr^{VI}$ and without using HF acid.

Figure 4:
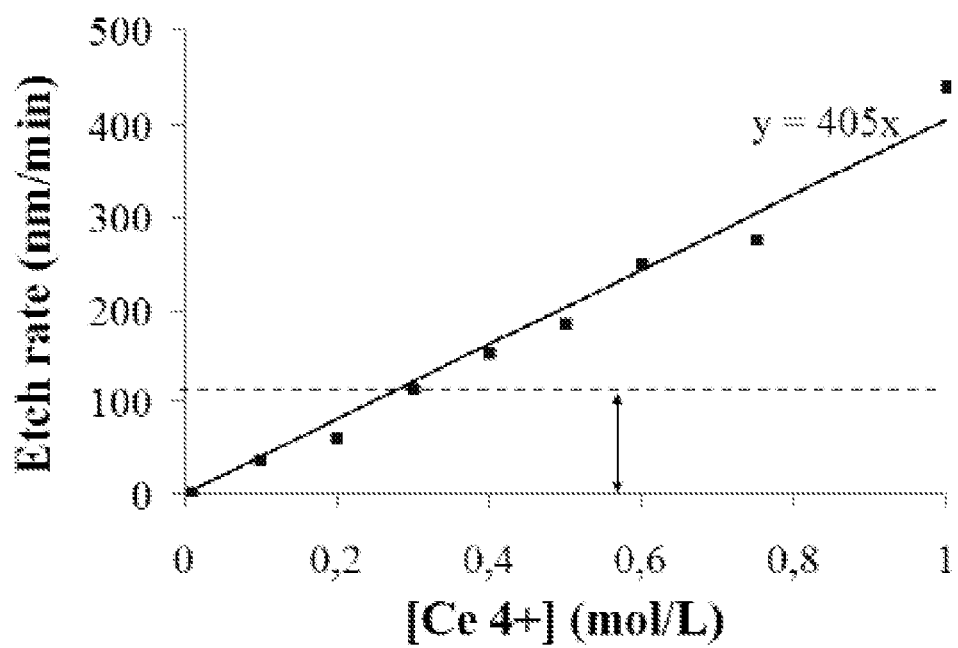
FIG. 4 shows the etch rate for a 1.5 μm thick Ge layer on Si(100) after etching in a $Ce^{4+}/H_2O$ solution according to embodiments of the present invention as a function of $Ce^{4+}$-concentration.

As already discussed, in order to characterize thin Ge layers with a thickness of between 20 nm and 10 μm, for example between 20 nm and 2 μm, between 20 nm and 1 μm or between 20 nm and 200 nm, it is advantageous to use an etchant exhibiting a relatively low etching rate (ER). The ER obtained for Ge layers in the $Ce^{4+}/H_2O$ solution according to the first embodiment of the invention shows a linear behaviour as a function of the $Ce^{4+}$-concentration (see FIG. 4). This indicates that the rate limiting step in the etching reaction is the oxidation of Ge surface atoms which is typical for etching with a preferential behaviour (e.g. anisotropic etching, defect etching). Moreover this shows that the oxidation kinetics of Ge atoms by $Ce^{4+}$ ions is of first order.

According to specific embodiments of the invention, the $Ce^{4+}$-concentration may be lower than 0.4 $mol \cdot L^{-1}$ in order to have good control on the etch depth. Good control on the etch depth may, according to these embodiments, be obtained because in these cases the ER is lower than 200 $nm \cdot min^{-1}$. For really thin Ge layer with a thickness of between 20 nm and 10 μm, for example between 20 nm and 2 μm, between 20 nm and 1 μm or between 20 nm and 200 nm, the ER may be between 4 and about 100 $nm \cdot min^{-1}$. A particularly useful range of etch rates for such really thin Ge layers is indicated by the region beneath the dashed line in FIG. 4. In these cases, the $Ce^{4+}/H_2O$ solution may comprise a $Ce^{4+}$-concentration of between 0.01 $mol \cdot L^{-1}$ and 0.3 $mol \cdot L^{-1}$. It is worth noting that, as can be seen from FIG. 4, for a $Ce^{4+}$-concentration of 0.01 $mol \cdot L^{-1}$, an ER of only 4 $nm \cdot min^{-1}$ may be obtained.

The selectivity S towards defects, e.g. threading dislocations, of a solution may be assessed by looking at the ratio of the lateral size of the etched figures (i.e. etch pits or hillocks) and the etch depth:

$$S = \frac{\text{width of etched figure}}{\text{etch depth}}$$

The selectivity S of the $Ce^{4+}/H_2O$ solution towards defects, e.g. threading dislocations, is independent of the $Ce^{4+}$-concentration and was determined to be approximately 1.

It has to be noted that the $Ce^{4+}/H_2O$ solution according to the first embodiment of the invention is liable to aging. In other words, the $Ce^{4+}/H_2O$ solution according to the first embodiment of the invention is unstable in time. Because of this aging the selectivity of the $Ce^{4+}/H_2O$ solution may be reduced as a function of time. Therefore, it is advantageous, to obtain good results, to always use freshly prepared $Ce^{4+}/H_2O$ solutions.

It has to be noted that similar results as described above for (100) samples can be obtained when using the $Ce^{4+}/H_2O$ etching solution according to the present embodiment for revealing defects on (111) samples.

According to a second embodiment of the present invention, the etching solution may comprise $MnO_4^-$ as an oxidizing agent and water as a solvent. Hence, the etching solution according to this second embodiment may be referred to as a $MnO_4^-/H_2O$ solution. As a source for $MnO_4^-$, for example potassium permanganate ($KMnO_4$) may be used. According to other embodiments, Magnesium permanganate, Sodium permanganate, Cesium permanganate may also be used as $MnO_4^-$-sources. The etching solution according to the second embodiment of the invention may comprise $MnO_4^-$ in a concentration of between 0.01 $mol \cdot L^{-1}$ and 0.6 $mol \cdot L^{-1}$.

According to embodiments of the invention, the $MnO_4^-/H_2O$ solution may comprise HF. HF may be present in the $MnO_4^-/H_2O$ solution in a concentration of between 0 $mol \cdot L^{-1}$ and 5 $mol \cdot L^{-1}$. Because of this low concentration of HF present, the $MnO_4^-/H_2O$ solution may still be environmentally and user friendly. According to other embodiments, although in these cases less environmentally and user friendly and not really contributing to improvement of the etching solution, the $MnO_4^-/H_2O$ solution may also comprise higher concentrations of HF. The presence of HF may increase the ER of the etching solution.

Hereinafter, the etching solution according to the second embodiment will further be described by means of some experiments. For these experiments, different amounts of $KMnO_4$ were dissolved in $H_2O$ so as to obtain different etching solutions with different $MnO_4^-$-concentrations. To some of the $MnO_4^-/H_2O$ solutions HF was added in different concentrations. Similarly as described for the first embodiment, etching was carried out at a 1.5 μm thick Ge layer on Si(100) and was performed by dipping 2×2 $cm^2$ samples in a beaker containing the etching solution. The solutions were always freshly prepared, unless otherwise mentioned. The samples were partially immersed in the etching solution so as to produce a step which was used for the determination of the ER. No stirring was applied to the solutions during etching and all experiments were performed at room temperature. After etching, the samples were thoroughly rinsed with DIW in order to immediately stop all reactions but also to clean the etched surface before further characterization. The samples were subsequently dried under $N_2$ flow. SEM was used as a characterization technique. Imaging of the etched surfaces before and after etching was done in a 45° tilted geometry whereas etch rate measurement was performed by doing cross-section measurements in the etched and non-etched regions.

Different compositions of the $MnO_4^-/H_2O$ solution with or without HF were evaluated with respect to their ability for revealing defects, e.g. threading dislocations in the Ge layers.

The $MnO_4^-$-concentration in the $MnO_4^-/H_2O$ solutions used ranged from 0.01 mol·L$^{-1}$ to 0.6 mol·L$^{-1}$. All solutions allowed revelation of the defects, e.g. threading dislocations but the best results were obtained with low concentration of $MnO_4^-$, i.e. concentrations of $MnO_4^-$ in the order of 0.01 mol·L$^{-1}$.

Figure 5:
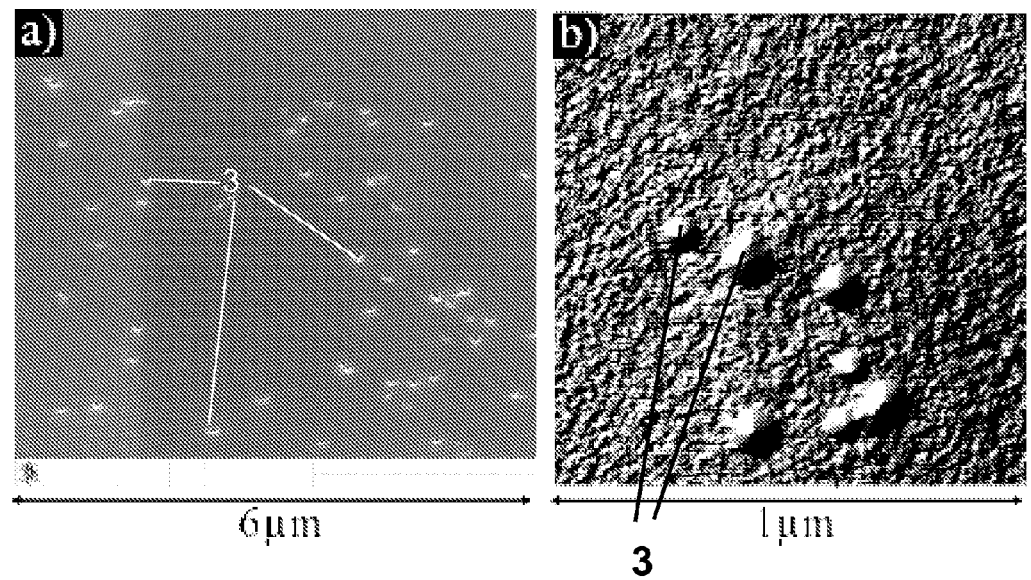
FIG. 5 shows SEM (left) and AFM (right) pictures of a 1.5 μm thick Ge layer on Si(100) after etching in a $MnO_4^-/HF/H_2O$ solution according to embodiments of the invention.

In all cases square pyramidal etch pits were obtained after etching but for high $MnO_4^-$-concentrations, the etch pits are rounded. Surface imaging (SEM (FIG. 5(a)) and AFM (FIG. 5(b))) of the Ge surface after etching in a solution containing 0.01 mol·L$^{-1}$ $MnO_4^-$ and 12.5 mol·L$^{-1}$ HF for 3 min is given as an illustration in FIG. 5.

The influence of the concentration of HF present in an $MnO_4^-/H_2O$ solution on the ability of defect revelation and ER was evaluated using a solution with a concentration of 0.01 mol·L$^{-1}$ of $MnO_4^-$. HF was added to the solutions so as to obtain $MnO_4^-/HF/H_2O$ solutions with concentrations of HF of 0 mol·L$^{-1}$, 0.5 mol·L$^{-1}$, 2.5 mol·L$^{-1}$, 5 mol·L$^{-1}$ and 12.5 mol·L$^{-1}$. Results with respect to TDD are summarized in FIG. 6. As can be observed form FIG. 6 and taking into account experimental errors (indicated by I in FIG. 6), the determined TDD of approximately $10^8/cm^2$ appears to be substantially independent of the HF concentration present in the solution and is in accordance with the results obtained with defect etching techniques using a prior art $CrO_3/HF/H_2O$ solution (see dashed line indicated with reference number 5 in FIG. 6) but also with TEM characterization.

Figure 7:
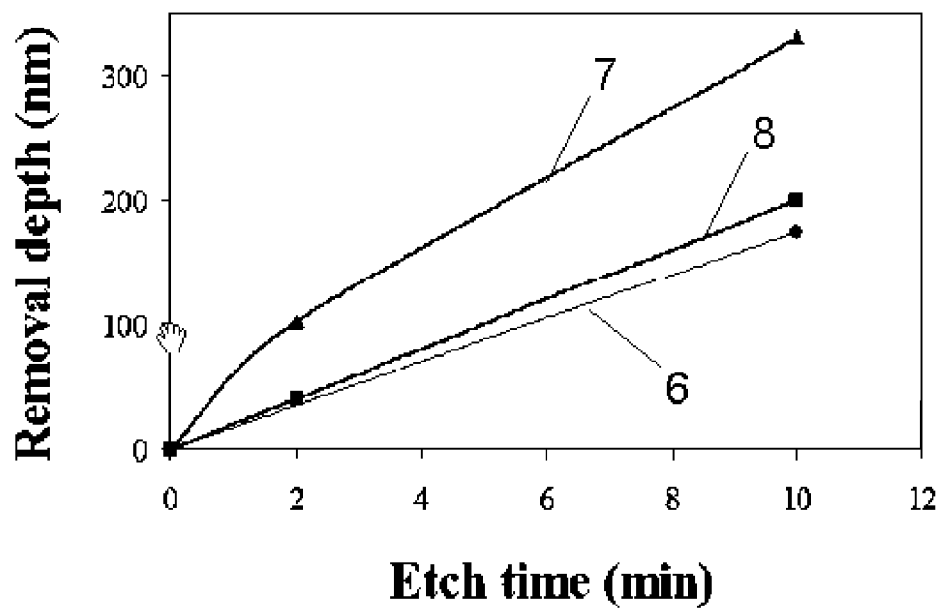
FIG. 7 shows etch depth as a function of etching time and as a function of HF-concentration for a 1.5 μm thick Ge layer after etching in a $MnO_4^-/HF/H_2O$ solution according to embodiments of the invention.

The ER of $MnO_4^-/H_2O$ solutions and $MnO_4^-/HF/H_2O$ solutions with different HF concentration was determined, all solutions having a $MnO_4^-$-concentration of 0.01 mol·L$^{-1}$. FIG. 7 illustrates removal depth as a function of etching time for these solutions. Curve 6 shows the ER for a solution comprising no HF, curve 7 shows the ER for a solution comprising 5 mol·L$^{-1}$ HF and curve 8 shows the ER for a solution comprising 12.5 mol·L$^{-1}$ HF. From FIG. 7 an ER of between 18 nm·min$^{-1}$ and 20 nm·min$^{-1}$ can be derived for solutions comprising 0 mol·L$^{-1}$ HF and 12.5 HF and an ER of 35 nm·min$^{-1}$ can be derived for solutions comprising 5 mol·L$^{-1}$ HF. From this it is clear that addition of HF increases the ER. However, when the concentration of HF becomes too high, the ER is decreased again.

The increase in ER by adding HF to the etching solution can be explained by two effects. HF may be more efficient in the dissolution of $GeO_2$ oxide but also the increase of the acidity of the solution drastically increases the oxidation potential of $MnO_4^-$ anions. However there is no obvious explanation for the higher ER obtained with 5 mol·L$^{-1}$ HF than for 12.5 mol·L$^{-1}$. With the etching solution according to the second embodiment of the invention an ER between 20 and 50 nm·min$^{-1}$ may be obtained depending the HF concentration. The low ER makes the etching solutions according to the second embodiments suitable to be used for easily revealing defects, e.g. threading dislocations in thin Ge layers with a thickness of between 20 nm and 10 μm, for example between 20 nm and 2 μm, between 20 nm and 1 μm or between 20 nm and 200 nm.

The selectivity S towards defects, e.g. threading dislocations of the $MnO_4^-/H_2O$ and $MnO_4^-/HF/H_2O$ solutions with a $MnO_4^-$ concentration of 0.01 mol·L$^{-1}$ is approximately 1 independent of the HF concentration, which is comparable to the results obtained for the etching solution according to the first embodiments of the invention.

Figure 6:
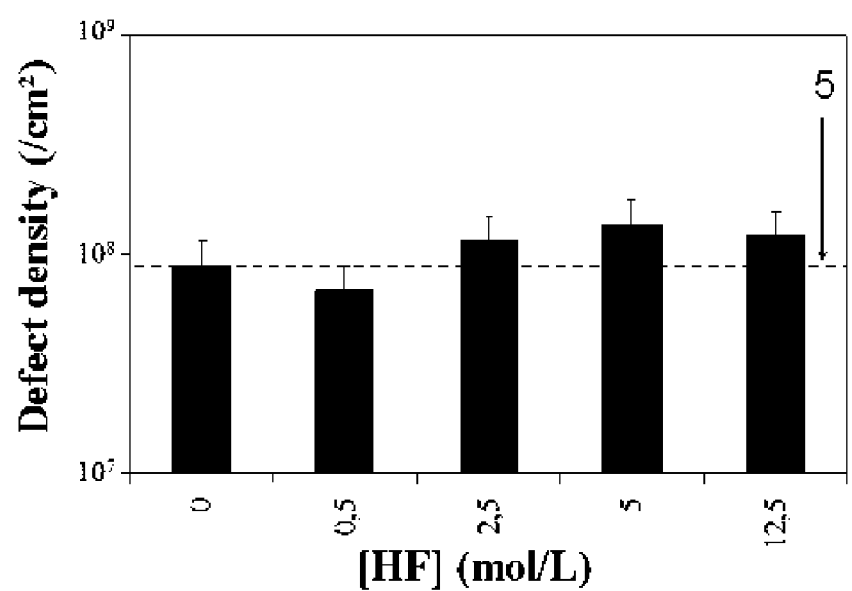
FIG. 6 shows the threading dislocation density for a 1.5 μm thick Ge layer after etching in a $MnO_4^-/HF/H_2O$ solution according to embodiments of the present invention with a $MnO_4^-$-concentration of 0.01 mol·L$^{-1}$ and for different HF-concentrations.

From the results illustrated in FIG. 6 and FIG. 7 it can be concluded that addition of HF is not required for obtaining a good etching solution exhibiting a relatively low ER and revealing defects, e.g. threading dislocations.

It has to be noted that similar results as described above for (100) samples can be obtained when using the $MnO_4^-/H_2O$ and $MnO_4^-/HF/H_2O$ etching solution according to the present embodiment for revealing defects on (111) samples.

Figure 8:
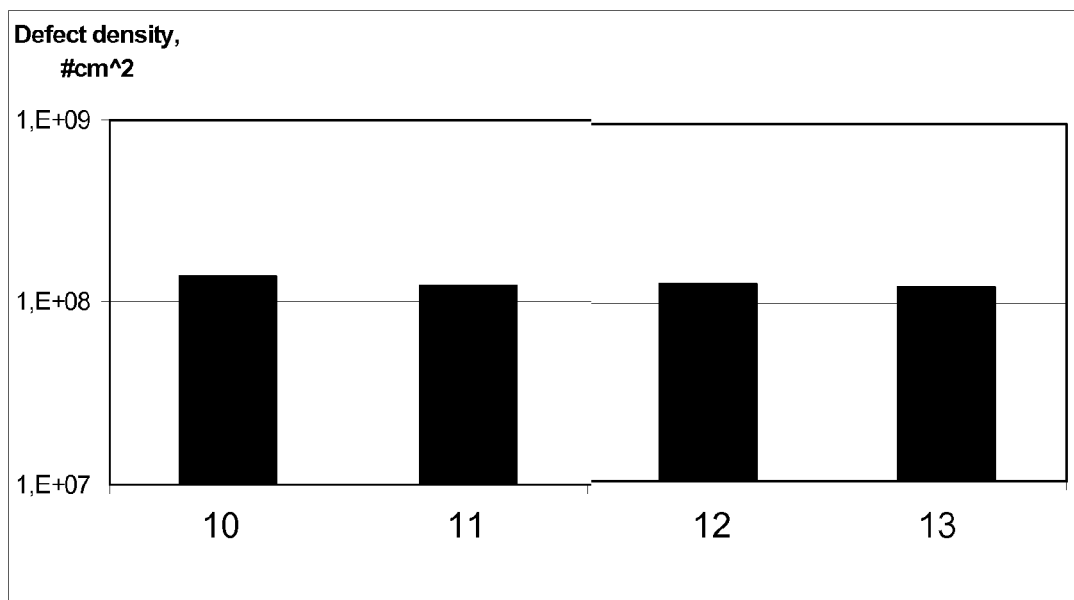
FIG. 8 shows the threading dislocation density for a 1.5 μm thick Ge layer after etching in different etching solutions according to embodiments of the invention.

Hereinafter some examples of etching solutions according to embodiments of the invention will be given. FIG. 8 illustrates the defect density for etching solutions according to embodiments of the present invention which exhibit a low ER and which may thus be suitable for revealing defects, e.g. threading dislocations in thin Ge layers with a thickness of between 20 nm and 10 μm, for example between 20 nm and 2 μm, between 20 nm and 1 μm or between 20 nm and 200 nm. A first example is a $Ce^{4+}/H_2O$ solution with a $Ce^{4+}$-concentration of 0.01 mol·L$^{-1}$. With this solution an ER of 3.5 nm·min$^{-1}$ was obtained. After etching for 10 minutes, defects, e.g. threading dislocations, are revealed with defect density of more than $10^8/cm^2$ (see curve indicated with reference number 10). A second example is a $Ce^{4+}/H_2O$ solution with a $Ce^{4+}$-concentration of 0.1 mol·L$^{-1}$. With this solution an ER of 40 nm·min$^{-1}$ was obtained. After etching for 3 minutes, defects, e.g. threading dislocations, are revealed with defect density of more than $10^8/cm^2$ (see curve indicated with reference number 11). A third example is a $MnO_4^-/HF/H_2O$ comprising 0.01 mol·L$^{-1}$ $MnO_4^-$, 10 ml HF and 40 ml $H_2O$. With this solution an ER of 50 nm·min$^{-1}$ was obtained. After etching for 2 minutes, defects, e.g. threading dislocations, are revealed with defect density of more than $10^8/cm^2$ (see curve indicated with reference number 12). A fourth example is a $MnO_4^-/HF/H_2O$ comprising 0.01 mol·L$^{-1}$ $MnO_4^-$, 25 ml HF and 25 ml $H_2O$. With this solution an ER of 20 nm·min$^{-1}$ was obtained. After etching for 2 minutes, defects, e.g. threading dislocations, are revealed with defect density of more than $10^8/cm^2$ (see curve indicated with reference number 13).

It is to be understood that although preferred embodiments, specific constructions and configurations, as well as materials, have been discussed herein for devices according to the present invention, various changes or modifications in form and detail may be made without departing from the scope of this invention as defined by the appended claims. For example, the etching solution may also be for revealing defects in a III-V semiconductor layer, e.g. a layer comprising GaAs or InP or a combination thereof such as e.g. GaInAs or GaInP. According to these embodiments, the present invention provides an etching solution for revealing defects a III-V semiconductor layer, e.g. GaAs or InP layer, the solution comprising:

an oxidizing agent comprising $Ce^{4+}$ or $MnO_4^-$, and
a solvent such as e.g. water.

The etching solution is able to exhibit an etch rate of between 4 nm·min$^{-1}$ and 450 nm·min$^{-1}$.

Similar results may be obtained for III-V semiconductor layers, e.g. layers comprising GaAs or InP or a combination thereof such as e.g. GaInAs or GaInP, with the etching solution according to embodiments of the invention as was described above in case of Ge layers.

The invention claimed is:

1. A method for revealing defects in a germanium layer or a III-V semiconductor layer, the method comprising immersing a substrate comprising the germanium layer or the III-V semiconductor layer in an etching solution consisting essentially of
(i) a $Ce^{4+}$ oxidizing agent or a $MnO4^-$ oxidizing agent; and
(ii) a solvent.

2. The method of claim 1, wherein the germanium layer or the III-V semiconductor layer has a thickness between 20 nm and 2 μm.

3. The method of claim 1, wherein the etching solution exhibits an etch rate of between 4 nm/min and 450 nm/min.

4. The method of claim 3, wherein the etching solution exhibits an etch rate between 4 nm/min and 200 nm/min.

5. The method of claim 1, wherein immersing the substrate comprising the germanium layer in the etching solution is for between 1.5 minutes and 10 minutes.

6. The method of claim 1, wherein the solvent is water.

7. The method of claim 1, wherein the etching solution consists essentially of the $Ce^{4+}$ oxidizing agent and the solvent.

8. The method of claim 7, wherein $Ce^{4+}$ oxidizing agent is present in a concentration of between 0.01 mol/L and 1 mol/L.

9. The method of claim 8, wherein $Ce^{4+}$ oxidizing agent concentration is less than 0.4 mol/L.

10. The method of claim 1, wherein the etching solution consists essentially of the $MnO_4^-$ oxidizing agent and the solvent.

11. The method of claim 10, wherein the $MnO_4^-$ oxidizing agent is present in a concentration of between 0.01 $mol \cdot L^{-1}$ and 0.6 $mol \cdot L^{-1}$.

12. The method of claim 1, wherein the substrate comprises a germanium layer.

13. The method of claim 1, wherein the substrate comprises a III-V semiconductor layer.

14. The method of claim 13, wherein the III-V semiconductor layer comprises GaAs, InP, GaInAs, or GaInP.

15. The method of claim 1 wherein the etching solution consists essentially of the solvent and a $Ce^{4+}$ oxidizing agent selected from the group consisting of cerium ammonium nitrate $((NH_4)_2Ce(NO_3)_6)$, ammonium cerium sulphate $(Ce(NH_4)_4(SO_4)_4)$ and cerium sulphate $(Ce(_8O_4)_2)$.

16. The method of claim 1 wherein the etching solution consists essentially of the solvent and a $MnO_4^-$ oxidizing agent selected from the group consisting of potassium permanganate, magnesium permanganate, sodium permanganate and cesium permanganate.

* * * * *